United States Patent [19]
Smith

[11] Patent Number: 4,902,227
[45] Date of Patent: Feb. 20, 1990

[54] DENTAL TREATMENT TRAY

[75] Inventor: Lawrence C. Smith, Sumner, Wash.

[73] Assignee: Pascal Company, Inc., Bellevue, Wash.

[21] Appl. No.: 190,104

[22] Filed: May 4, 1988

[51] Int. Cl.⁴ ............................................. A61C 5/00
[52] U.S. Cl. ................................... 433/215; 433/42; 128/136
[58] Field of Search .................... 433/215, 42, 43, 45, 433/37; 128/62 A, 66, 861

[56] References Cited

U.S. PATENT DOCUMENTS

| Re. 28,667 | 12/1975 | Gores | 128/136 |
|---|---|---|---|
| 730,658 | 6/1903 | Huber | 433/42 |
| 1,146,264 | 7/1915 | Kelly | 433/42 |
| 2,352,545 | 6/1944 | Jefferies | 433/45 |
| 2,857,909 | 10/1958 | Johnson | 128/136 |
| 4,173,219 | 11/1979 | Lentine | 128/136 |
| 4,376,628 | 3/1983 | Aardse | 433/80 |
| 4,475,888 | 10/1984 | Gores et al. | 433/42 |

FOREIGN PATENT DOCUMENTS

| 520556 | 2/1933 | Fed. Rep. of Germany | 433/43 |
|---|---|---|---|
| 7709035 | 2/1979 | Netherlands | 128/136 |

OTHER PUBLICATIONS

Dental Economics magazine, Jul., 1979, a Coe Laboratories ad showing several impression trays.
Dental Hygiene magazine, vol. 53, No. 7, Jul., 1979, p. 334.
RDH magazine, Jul./Aug. 1986, p. 44.
Dental Hygiene magazine, vol. 53, No. 6, Jun., 1979, Sybron/Kerr ad for a disposable fluoride tray.
The Journal of the American Dental Association, vol. 98, No. 2, Feb., 1979, Cutter Laboratory ad showing an impression tray.
The Journal of the American Dental Association, vol. 98, No. 3, Mar., 1979, Coe Laboratories ad showing an impression tray.

*Primary Examiner*—John J. Wilson
*Attorney, Agent, or Firm*—Gregory W. Moravan

[57] ABSTRACT

A molded, one-piece plastic dental treatment tray for applying fluoride or other medication to a patient's teeth. The tray has a pair of elongated locking flanges on one of its handles which engage the lateral edges of the other of its handles to hold the tray folded up with its two teeth receiving troughs in an aligned, assembled relationship. At least one of the handles is molded at an angle with respect to the bottom of its trough to help ensure that when the tray is folded up, the free ends of its troughs are urged into contact with each other, to enable the tray to be inserted more easily into the patient's mouth. The bottoms of the troughs are flat and smooth enough for them to move easily over each other in any direction while in the patient's mouth, so the tray will better accommodate any individual differences in the mouth, jaws or teeth of the particular patient.

12 Claims, 2 Drawing Sheets

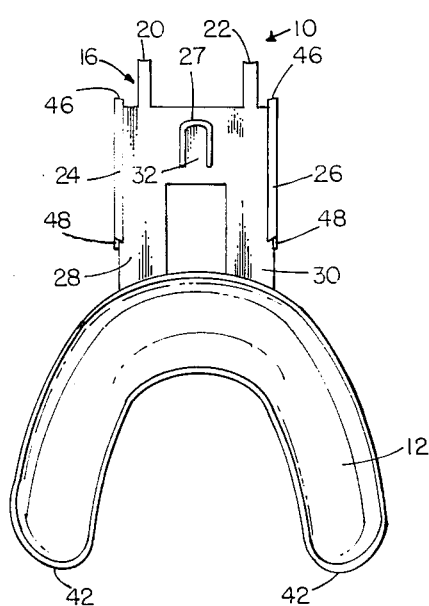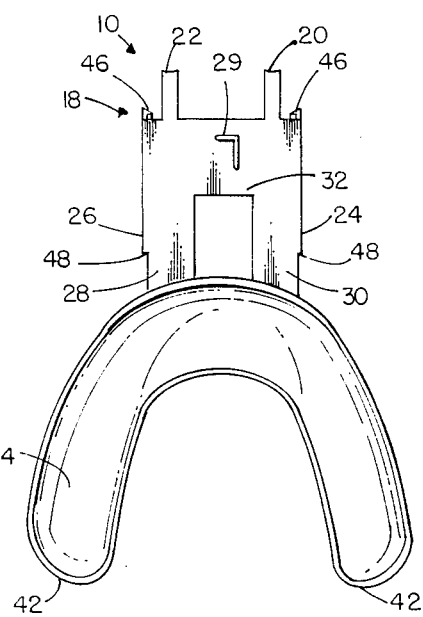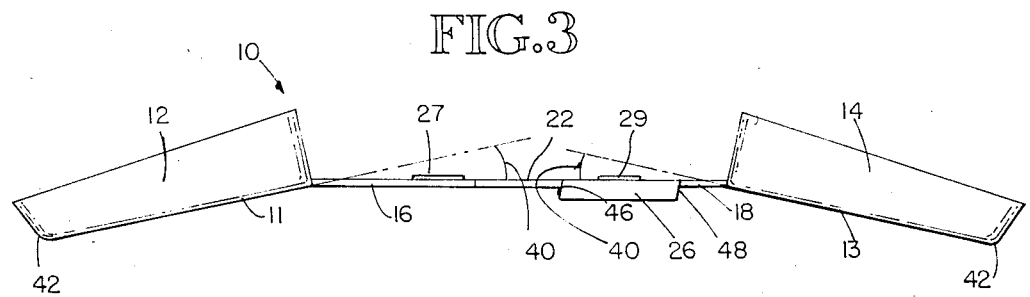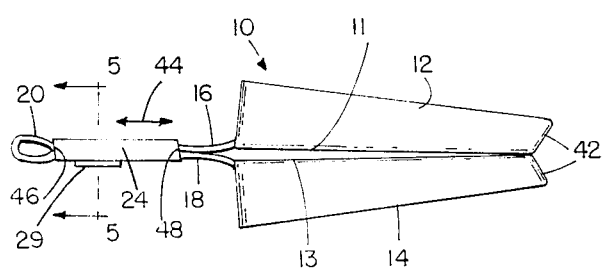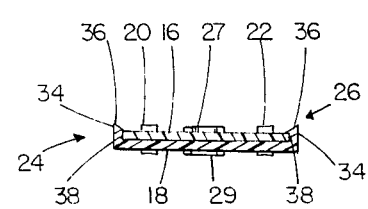

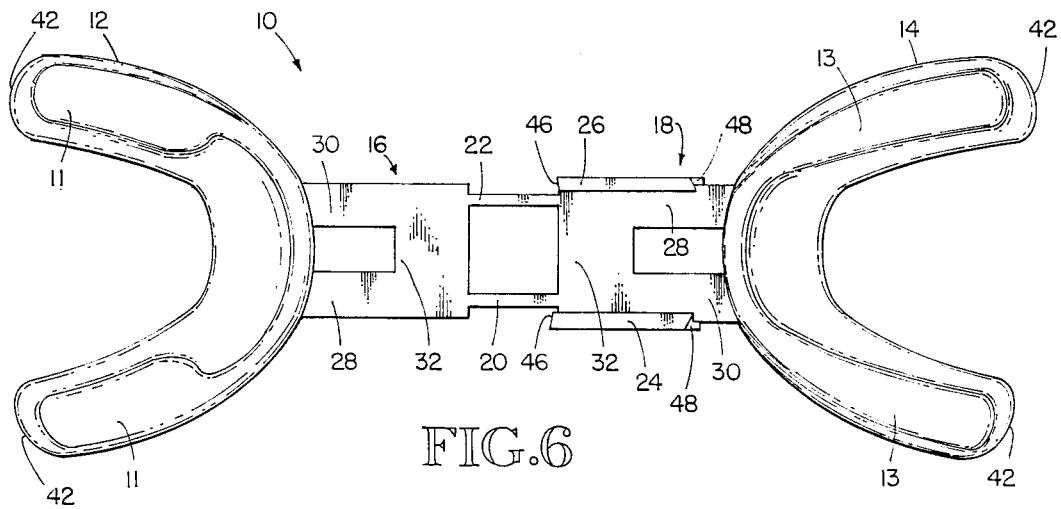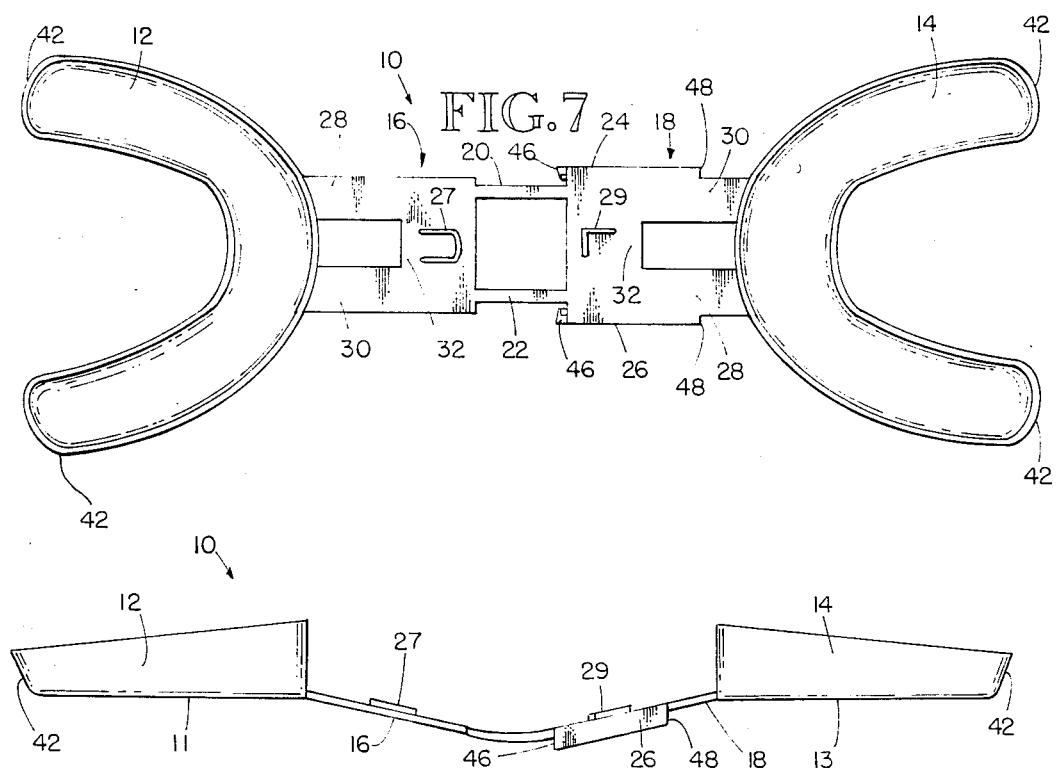

DENTAL TREATMENT TRAY

BACKGROUND OF THE INVENTION

The present invention relates to the field of dental care, and more particularly, it relates to a dental treatment tray for applying fluoride or other medications to the teeth of a patient.

SUMMARY OF THE INVENTION

Some of the objects of the present invention are to provide a disposable dental treatment tray which is relatively inexpensive, which provides handles by which it is easily manipulated by the dentist, which fits easily and comfortably into the patient's mouth, and which permits its troughs to be moved relative to each other in all directions generally in the planes of the bottoms of the troughs while in the patient's mouth to help to accommodate individual mouth differences for greater patient comfort.

In basic form, the present invention comprises a pair of U-shaped troughs for holding the medication. One trough is sized and shaped to receive the patient's upper teeth, while the other trough is sized and shaped to receive the patient's lower teeth. Each trough has a broad, flat handle which extends outwardly from the center of the bottom of the trough, and which is sized to be conveniently manipulated by the dentist. The handles are preferably interconnected to keep the pair of troughs together during manufacture, storage and use. The tray is preferably made from soft, resilient plastic for greater patient comfort.

The tray is held folded for use by a pair of elongated locking flanges on one of the tray's handles which releasably hold the lateral edges of the other handle. The handles are molded at a small angle with respect to the troughs to help ensure that when the tray is folded for use, the free ends of the troughs will be urged into contact with each other so the tray can be more easily inserted into the patient's mouth. Preferably, the bottoms of the troughs are unobstructed and are smooth enough so that when the folded tray is in the patient's mouth, the troughs can be moved with respect to each other in all directions generally in the planes of the bottoms of the troughs to accomodate individual differences in the mouths of patients, for greater patient comfort.

The foregoing is intended to be but a brief summary of, and not a detailed catalog of, the various objects, features, advantages and characteristics of the present invention, since these and further objects, features, advantages and characteristics will be expressly or inherantly disclosed to those skilled in the art to which it pertains, in view of all of the disclosures herein.

BRIEF DESCRIPTION OF THE FIGURES

FIG. 1 is a top plan view of the present invention shown folded for use;

FIG. 2 is a bottom view of the present invention shown folded for use;

FIG. 3 is a side elevation view of the present invention shown unfolded;

FIG. 4 is a side elevation view of the present invention shown folded for use;

FIG. 5 is a cross sectional view taken along line 5—5 of FIG. 4.

FIG. 6 is a bottom plan view of the present invention shown unfolded;

FIG. 7 is a top plan view of the present invention shown unfolded; and

FIG. 8 is a side elevation view of the present invention shown in the position it has while being molded.

DESCRIPTION OF THE PREFERRED EMBODIMENTS

Referring now to the figures, the dental treatment tray of the present invention is generally designated at 10. The tray 10 comprises a pair of generally U-shaped troughs 12, 14; a pair of handles 16, 18; a pair of connectors 20, 22; and a pair of elongated locking flanges 24, 26.

Each trough 12, 14 is of conventional construction, is large enough to accomodate a full set of teeth, and is deep enough to receive the patient's teeth at least to their gum lines. Although only one size of tray 10 with its trough 12, 14 is illustrated, it is understood that tray 10 with its troughs 12, 14 can be made in any size appropriate for the needs of any particular patient.

In order to provide troughs 12, 14 which are as comfortable as possible, it is preferred that the interiors of the troughs be molded in the general shape of a typical set of human upper and lower teeth, with trough 12 being shaped to receive the patient's upper teeth and trough 14 being shaped to receive the patient's lower teeth. Since human upper and lower teeth are different, it is preferred that indicia 27 (U for upper), 29 (L for lower) be placed on handles 16, 18, respectively. Since indicia 27, 29 have sharp edges, as seen, they also serve the dual purpose of providing finger grips for the dentist using tray 10.

Handles 16, 18 are held together by lateral connectors 20, 22. Each handle 16, 18 comprises two elongated lateral legs 28, 30 between the ends of which extends a transverse handle piece 32. Locking flanges 24, 26 extend along the sides of handle 18. Each locking flange 24, 26 has a side 34 and an inclined top 36. The side 34 and top 36 of each locking flange 24, 26 defines, in conjunction with handle 18, a generally U-shaped locking recess 38.

Preferably tray 10 is injection molded in one piece from any suitable soft, resilient plastic. Referring now to FIG. 8, it shows tray 10 in the position it has while being molded. Ends 46, 48 of locking flanges 24, 26 are intentionally inclined with respect to the plane of handle 18 so they are actually vertical while molded, to facilitate making the mold for tray 10 and its locking flanges 24, 26.

In order to prepare tray 10 for use, medication is first added to troughs 12, 14. Tray 10 is then folded so handle 16 and trough 12 are directly over handle 18 and trough 14. Then handles 16, 18 are urged towards each other until the lateral edges of handle 16 snap into locking recesses 38 of the locking flanges 24, 26 of handle 18, as best seen in FIGS. 4 and 5. The inclined tops 36 of locking flanges 24, 26 aid in this process since as handles 16, 18 are urged towards each other, the lateral edges of handle 16 slide down the inclined tops 36 of locking flanges 24, 26, thereby forcing the resilient sides 34 of locking flanges 24, 26 away from each other. As handle 16 is urged further towards handle 18, the lateral edges of handle 16 eventually clear the inside edges of the inclined tops 36 of locking flanges 24, 26, at which time the resilient sides 34 of locking flanges 24, 26 urge the inclined tops 36 inwardly towards each other over the top surface of handle 16, thereby securing handle 16 in place with its lateral edges engaged in locking recesses 38.

The resiliency of locking flanges 24, 26 aid in this process since it helps to permit such movement of the resilient sides 34 of the locking flanges 24, 26 first away from and then towards each other as handle 16 is snapped into place in locking recesses 38. Similarly, the resiliency of handle 16 permits it to bow slightly as it is being urged past the inclined tops 36 of locking flanges 24, 26. This bowing helps the lateral edges of handle 16 to clear inclined tops 36. However once the lateral edges of handle 16 are engaged in locking recesses 38, this same resiliency causes handle 16 to tend to resume its original unbowed configuration, thereby helping to lock its lateral edges firmly into locking recesses 38.

Locking flanges 24, 26 are sized long enough to securely hold handles 16, 18 and troughs 12, 14 in an aligned relationship as seen in FIGS. 1 and 2, and may be, by way of non-limiting example, about one inch long.

Preferably, the exterior bottoms 11, 13 of troughs 12, 14 are unobstructed and smooth enough to permit them to move, one on top of the other, in all directions generally in the planes of bottoms 11, 13. Such movement is permitted by the flexibility of locking flanges 24, 26 and handles 16, 18; and is aided by the physical construction of locking flanges 24, 26 which, while they are holding handle 16, are designed to allow handles 16, 18 to move relative to each other in the directions of double headed arrow 44, as seen in FIG. 4. Such movement is made easier by molding a fine texture into the portions of the surfaces of handles 16, 18 and locking flanges 24, 26 which are in contact with each other when the dental treatment tray 10 is folded up for use as seen in FIGS. 4 and 5. Such movement helps provide greater patient comfort since such movement will permit the patient to easily adjust troughs 12, 14 with respect to each other while they are in his mouth, as needed by the structure of his mouth, which will naturally vary somewhat from patient to patient.

To disengage handle 16 from its locking recesses 38, troughs 12, 14 are simply pulled away from each other until the lateral edges of handle 16 pull free of their locking recesses 38. This process is aided by the flexibility and resiliency of handles 16, 18 and locking flanges 24, 26.

As best seen in FIG. 3, handles 16, 18 are each molded at a slight angle 40 with respect to the bottom 11, 13 of troughs 12, 14. Angle 40, may be, by way of non-limiting example, about 12 to 15 degrees. The purpose of molding handles 16, 18 at angle 40 is, as best seen in FIG. 4, to help ensure that when tray 10 is folded for use, the free ends 42 of troughs 12, 14 are urged into contact with each other so tray 10 may be inserted into the patient's mouth more easily. The resiliency of handles 16, 18 is important here too, since if the free ends 42 of troughs 12, 14 are inadvertently moved away from each other, such resiliency will tend to urge them back towards each other. Angle 40 is preferably selected to be just large enough to produce this result, since angles 40 which are larger might tend to unsnap handle 16 from locking recesses 38, or might tend to cause the fronts of troughs 12, 14 adjacent to handles 16, 18 to separate from each other to an extent which could make insertion of the fronts of troughs 12, 14 into the patient's mouth more difficult or uncomfortable.

After use, tray 10 can either be discarded, or it can be cleaned and sterilized in preparation for reuse.

From the foregoing, various further applications, modifications and adaptations of the apparatus disclosed by the foregoing preferred embodiments of the present invention will now be apparent to those skilled in the art to which it pertains, within the scope of the following claims.

What is claimed is:

1. A dental treatment tray for applying medication to a patient's teeth, wherein said tray comprises:
   a pair of troughs; wherein each of said troughs has an exterior trough bottom; wherein one of said troughs is sized to receive said patient's upper teeth; wherein the other of said troughs is sized to receive said patient's lower teeth; and wherein said troughs are also sized to be adapted to receive said medication;
   a resilient trough handle extending outwardly from each trough; and
   a pair of resilient elongated locking flanges;
   wherein each of said locking flanges extends along a respective lateral edge portion of one of said trough handles; wherein each of said locking flanges defines an elongated locking recess that is sized and shaped to be adapted to receive a corresponding lateral edge of the other of said handles; wherein each of said locking flanges is sized and shaped to be adapted to resiliently engage its said corresponding lateral edge of the other of said handles in its said elongated locking recess, to releasably hold said troughs in an assembled relationship with said trough bottoms facing each other; and wherein when each of said locking flanges has engaged its said corresponding lateral edge of the other of said handles, a top portion of each of said locking flanges extends over a corresponding top portion of its said corresponding lateral edge of the other of said handles.

2. A dental treatment tray according to claim 1, wherein said tray further comprises at least one connector connecting said trough handles.

3. A dental treatment tray according to claim 1, wherein said tray further comprises a pair of laterally located connectors connecting said trough handles; wherein said pair of connectors are flexible; and wherein said pair of connectors are integrally formed in one piece with said trough handles.

4. A dental treatment tray according to claim 1, wherein said dental treatment tray has a folded configuration in which said troughs are in said assembled relationship with said trough bottoms facing each other; wherein said dental treatment tray has an unfolded configuration in which said trough bottoms do not face each other; wherein each of said troughs has a pair of free ends; and wherein, when said dental treatment tray is in said unfolded configuration, at least one of said trough handles extends at an angle with respect to a plane of its respective said trough bottom, to help ensure that when said troughs are in said assembled relationship said free ends of said troughs are urged into contact with each other, to help said tray to be more easily inserted into said patient's mouth.

5. A dental treatment tray according to claim 1, wherein each of said exterior trough bottoms is unobstructed and smooth enough to permit them to move freely over each other in any direction generally in the planes of said trough bottoms when said tray is in said assembled relationship in said patient's mouth, to help permit said troughs to be moved with respect to each other to better accommodate any particular characteristics of said patient's mouth, jaws and teeth, for greater patient comfort.

6. A dental treatment tray according to claim 1, wherein said trough handles and said locking flanges have a portion of their surfaces in contact with each other when said troughs are in said assembled relationship; and wherein said portion of their surfaces has a fine texture to help enable said portions of said surfaces to move relative to each other during use of said dental treatment tray.

7. A dental treatment tray for applying medication to a patient's teeth, wherein said tray comprises:
- a pair of troughs; wherein each of said troughs has an exterior trough bottom; wherein one of said troughs is sized to receive said patient's upper teeth; wherein the other of said troughs is sized to receive said patient's lower teeth; and wherein said troughs are also sized to be adapted to receive said medication;
- a resilient trough handle extending outwardly from each trough; and
- means for holding said handles and said troughs in an assembled relationship with said trough bottoms facing each other;
- wherein said dental treatment tray has a folded configuration in which said troughs are in said assembled relationship with said trough bottoms facing each other; wherein said dental treatment tray has an unfolded configuration in which said trough bottoms do not face each other;
- wherein each of said troughs has a pair of free ends; and
- wherein, when said dental treatment tray is in said unfolded configuration, at least one of said trough handles extends at an angle with respect to a plane of its respective said trough bottom, to help ensure that when said troughs are in said assembled relationship said free ends of said troughs are urged into contact with each other, to help said tray to be more easily inserted into said patient's mouth.

8. A dental treatment tray according to claim 7, wherein said means for holding comprises a pair of resilient elongated locking flanges; wherein each of said locking flanges extends along a respective lateral edge portion of one of said trough handles; and wherein each of said locking flanges defines an elongated locking recess that is sized and shaped to be adapted to receive a corresponding lateral edge of the other of said handles; wherein each of said locking flanges is sized and shaped to be adapted to resiliently engage its said corresponding lateral edge of the other of said handles in its said elongated locking recess, to releasably hold said troughs in said assembled relationship; and wherein when each of said locking flanges has engaged its said corresponding lateral edge of the other of said handles, a top portion of each of said locking flanges extends over a corresponding to portion of its said corresponding lateral edge of the other of said handles.

9. A dental treatment tray according to claim 8, wherein said trough handles and said locking flanges have a portion of their surfaces in contact with each other when said troughs are in said assembled relationship; and wherein said portion of their surfaces has a fine texture to help enable said portions of said surfaces to move relative to each other during use of said dental treatment tray.

10. A dental treatment tray according to claim 7, wherein said tray further comprises at least one connector connecting said trough handles.

11. A dental treatment tray according to claim 7, wherein said tray further comprises a pair of laterally located connectors connecting said trough handles; wherein said pair of connectors are flexible; and wherein said pair of connectors are integrally formed in one piece with said trough handles.

12. A dental treatment tray according to claim 7, wherein each of said exterior trough bottoms is unobstructed and smooth enough to permit them to move freely over each other in any direction generally in the planes of said trough bottoms when said tray is in said assembled relationship in said patient's mouth, to help permit said troughs to be moved with respect to each other to better accommodate any particular characteristics of said patient's mouth, jaws and teeth, for greater patient comfort.

* * * * *